(12) United States Patent
Al-Muthana et al.

(10) Patent No.: US 9,405,037 B2
(45) Date of Patent: Aug. 2, 2016

(54) METHODS FOR DETERMINING WETTABILITY FROM NMR

(71) Applicants: Ahmed Al-Muthana, Dhahran (SA); Gabor Hursan, Dhahran (SA); Shouxiang Ma, Dhahran (SA); Philip M. Singer, Richmond, TX (US); Benjamin Nicot, Rio De Janeiro (BR); Andrea Valori, Al-Khobar (SA); Farhan Ali, Dammam (SA); Henry N. Bachman, Missouri City, TX (US)

(72) Inventors: Ahmed Al-Muthana, Dhahran (SA); Gabor Hursan, Dhahran (SA); Shouxiang Ma, Dhahran (SA); Philip M. Singer, Richmond, TX (US); Benjamin Nicot, Rio De Janeiro (BR); Andrea Valori, Al-Khobar (SA); Farhan Ali, Dammam (SA); Henry N. Bachman, Missouri City, TX (US)

(73) Assignees: SCHLUMBERGER TECHNOLOGY CORPORATION, Sugar Land, TX (US); SAUDI ARAMCO, Dhahran (SA)

( * ) Notice: Subject to any disclaimer, the term of this patent is extended or adjusted under 35 U.S.C. 154(b) by 674 days.

(21) Appl. No.: 13/854,183

(22) Filed: Apr. 1, 2013

(65) Prior Publication Data

US 2013/0261979 A1    Oct. 3, 2013

Related U.S. Application Data

(60) Provisional application No. 61/619,144, filed on Apr. 2, 2012.

(51) Int. Cl.
*G01N 15/00* (2006.01)
*G01V 3/38* (2006.01)
(Continued)

(52) U.S. Cl.
CPC ............. *G01V 3/38* (2013.01); *G01N 24/081* (2013.01); *G01V 3/14* (2013.01)

(58) Field of Classification Search
CPC ............. G01N 13/00; G01N 15/08; G01N 2013/0208; G01N 24/081; G01N 7/04; G01V 3/14; G01V 3/38
See application file for complete search history.

(56) References Cited

U.S. PATENT DOCUMENTS

| 5,387,865 A * | 2/1995 | Jerosch-Herold ...... G01N 15/08 324/300 |
| 6,765,380 B2 | 7/2004 | Freedman et al. |

(Continued)

FOREIGN PATENT DOCUMENTS

| CN | 101915716 A | 12/2010 |
| WO | 2010126998 A2 | 11/2010 |
| WO | 2011091269 A2 | 7/2011 |

OTHER PUBLICATIONS

Anderson, "Wettability Literature Survey-Part 6: The Effects of Wettability on Waterflooding", Journal of Petroleum Technology, vol. 39, No. 12, 1987, pp. 1605-1622.

(Continued)

*Primary Examiner* — Elias Desta
(74) *Attorney, Agent, or Firm* — Bridget M. Laffey

(57) ABSTRACT

Methods are described for wettability characterization based on NMR measurements, which are sensitive to the surface wetting conditions of oil and water at the pore scale. The described methods make use of surface relaxation effects on the NMR relaxation ($T_2$). Workflows are described to obtain wettability profiles of a porous media such as a rock either in the native state or prepared to a certain state in the laboratory. An underlying forward model is also described for the mixed wet and fractionally saturated pore spectrum. Outputs of the described inversion include continuous saturation and wettability profiles as a function of the pore sizes in the porous media, as well as an averaged value for saturation and wettability over the entire pore spectrum.

35 Claims, 12 Drawing Sheets

(51) Int. Cl.
*G01V 3/14* (2006.01)
*G01N 24/08* (2006.01)

(56) References Cited

U.S. PATENT DOCUMENTS

| | | | |
|---|---|---|---|
| 6,883,702 | B2 | 4/2005 | Hurlimann et al. |
| 2006/0272812 | A1* | 12/2006 | Yu .................. G01N 24/081 166/252.5 |
| 2006/0273788 | A1 | 12/2006 | Georgi et al. |
| 2010/0237860 | A1 | 9/2010 | Hurlimann et al. |
| 2011/0181277 | A1 | 7/2011 | Korb et al. |

OTHER PUBLICATIONS

Brownstein, et al., "Importance of classical diffusion in NMR studies of water in biological cells", Phys. Rev. A., vol. 19, Jun. 1, 1979, pp. 2446-2453.

Carr, et al., "Effects of Diffusion on Free Procession in Nuclear Magnetic Resonance Experiments", Physical Review, vol. 94, No. 3, May 1, 1954, pp. 630-638.

Donaldson, et al., "Wettability Determination and its Effect on Recovery Efficiency", SPE Journal, vol. 9, No. 1, 1969, pp. 13-20.

Lo, et al., "Mixing Rules and Correlations of NMR Relaxation Time With Viscosity, Diffusivity, and Gas/Oil Ratio of Methane/Hydrocarbon Mixtures", SPE-77264—SPE Journal vol. 7, No. 1, 2002, pp. 24-34.

Looyestijn, et al., "Wettability Index Determination by Nuclear Magnetic Resonance", SPE 93624—14th SPE Middle East Oil and Gas Show and Conference, Kingdom of Bahrain, Mar. 12-15, 2005, 8 pages.

Looyestijn, et al., "Wettability-Index Determination by Nuclear Magnetic Resonance", SPE 93624-PA—Reservoir Evaluation & Engineering, vol. 9(2), 2006, pp. 146-153.

Ma, et al., "Characterization of wettability from spontaneous imbibition measurements", Journal of Canadian Petroleum Technology, vol. 38, No. 13, 1999, pp. 1-8.

Ma, et al., "Effect of contact angle on drainage and imbibition in regular polygonal tubes", Colloids and Surfaces A: Physicochemical and Engineering Aspects, vol. 117, Issue 3, Oct. 20, 1996, pp. 273-291.

Masalmeh, et al., "Improved Characterisation and Modelling of Carbonate Reservoirs for Predicting Waterflood Performance", IPTC-11722—International Petroleum Technology Conference, Dubai, Dec. 4-6, 2007, 14 pages.

Meiboom, et al., "Modified SpinEcho Method for Measuring Nuclear Relaxation Times", Review of Scientific Instruments, vol. 29, No. 8, 1958, pp. 688-691.

Okasha, et al., "Fifty Years of Wettability Measurements in the Arab-D Carbonate Reservoir", SPE-105114—SPE Middle East Oil and Gas Show and Conference, Kingdom of Bahrain, Mar. 11-14, 2007, pp. 1-12.

Salathiel, "Oil Recovery by Surface Film Drainage in Mixed-Wettability Rocks", SPE 4104—Journal of Petroleum Technology, vol. 25, No. 10, 1973, 9 pages.

Venkataramanan, et al., "Mellin transform of CPMG data", Journal of Magnetic Resonance, vol. 206, No. 1, Sep. 2010, pp. 20-31.

Venkataramanan, et al., "Solving Fredholm Integrals of the First Kind With Tensor Product Structure in 2 and 2.5 Dimensions", IEEE Transactions on Signal Processing, vol. 5, No. 5, May, 2002, pp. 1017-1026.

International Search Report and Written Opinion issued in PCT/US2013/034928 on Oct. 10, 2013, 10 pages.

Al-Mahrooqi, S. H., et al., "Pore-Scale Modelling of NMR Relaxation for the Characterization of Wettability", Journal of Petroleum Science and Engineering, Elsevier, Amsterdam, NL, vol. 52, No. 1-4, (Jun. 1, 2006) pp. 172-186.

\* cited by examiner $S_i=1, W_i=1$
Before Oil Migration: $S_w=1$ $S_i=0.2, W_i=0.6$
After Oil Migration: $S_w=S_{wirr}$ $S_i=0.7, W_i=0.5$
After Waterflooding: $S_w=1-S_{or}$

METHODS FOR DETERMINING WETTABILITY FROM NMR

CROSS REFERENCE TO RELATED APPLICATION

This application claims the benefit of U.S. Provisional Patent Application Ser. No. 61/619,144 filed Apr. 2, 2012, which is incorporated herein by reference in its entirety.

FIELD

The subject disclosure generally relates to methods for determining wettability from nuclear magnetic resonance (NMR) measurements and other data. In particular, the subject disclosure relates to inversion-based methods for determining wettability and saturation over a range of pore sizes.

BACKGROUND

The wettability of the rock in an oil reservoir affects the saturations, capillary pressures (Pc), electrical properties, relative permeability and ultimate hydrocarbon recovery. In the petroleum industry, semi-empirical indices based on Pc curve measurements are used to describe core plug wettability: (1) Amott or Amott-Harvey index $I_{AH}$, and (2) U.S. Bureau of Mines (USBM) index, $I_{USBM}$. Frequently those indices do not match, despite industry expectation.

NMR is a technique that has been shown to be very sensitive to rock/fluid interfaces. The most widely used application is the measurement of the pore size distribution when the pores are all 100% saturated with a single phase such as water. In such cases, the interpretation is straightforward and is based on the fact that as the pore size decreases, the surface to volume ratio increases resulting in shorter (i.e., enhanced) $T_2$ relaxation times. It is also well known that the NMR $T_2$ relaxation times are highly sensitive to the presence of fractionally saturated (oil and water) and mixed wet pores, such as in the case of core-plugs in their native state taken from an oil zone.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method for characterizing wettability of a porous media is described. The method includes: receiving pore size distribution data representing a distribution of pore sizes within the porous media; receiving NMR data (e.g., echo train data) from a bulk aqueous fluid; receiving NMR data from a bulk oil; and performing an inversion on the NMR data using a forward model for pore level distribution of wettability and saturation in mixed wet conditions over a plurality of pore sizes using the pore size distribution data and the NMR data for the bulk aqueous fluid and bulk oil, thereby generating a wettability profile for the aqueous and/or oil fluids over a plurality of pore sizes of the porous media. According to some embodiments, the inversion is performed in the time domain, and the NMR data is of a type such as CPMG, diffusion editing, $T_1$-$T_2$, $T_2$, $T_2$-$T_2$ D-$T_1$ and D-$T_2$. The forward model can include a function for saturation that is either monotonically or non-monotonically increasing or decreasing along a spectrum of pore sizes, and the inversion can include mathematically constraining saturation values across a plurality of pore sizes in the forward model, for example based on a known saturation history of the porous media. According to some embodiments, overall wettability can be determined by integrating the wettability profile weighted by the pore size distribution data and/or overall saturation can be determined by integrating the saturation profile weighted by the pore size distribution data. According to some other embodiments, the inversion is performed in domains other than the time domain (e.g., in the T2 domain).

According to some embodiments a system for characterizing wettability of a porous media is described. The system includes: an NMR measurement system adapted and configured to make NMR measurements of a bulk aqueous fluid and a bulk oil, and to generate therefrom NMR data; and a processing system programmed and configured to perform an inversion on the NMR data using a forward model for pore level distribution of wettability and saturation in mixed wet conditions over a plurality of pore sizes using a pore size distribution of the porous media, and the NMR data, thereby generating a wettability profile for the aqueous fluid over a plurality of pore sizes of the porous media. According to some embodiments, the porous media is a core sample from a subterranean hydrocarbon-bearing formation, for example obtained using a core sampling tool deployable in a wellbore. According to some embodiments, at least part of the NMR measurement system is adapted to be deployed downhole so as to make the NMR measurements of the bulk aqueous fluid and/or bulk oil downhole while the fluid is in a live state.

This disclosure describes a laboratory based wettability characterization method based on NMR measurements, which are uniquely sensitive to the surface wetting conditions of oil and water at the pore scale. The subject disclosure exploits the well-known surface relaxation effects on the NMR relaxation ($T_2$). A new workflow to obtain the NMR wettability of a porous media such as a rock either in the native state or prepared to a certain state in the laboratory is disclosed. A new underlying forward model for the mixed wet and fractionally saturated $T_2$ distribution is also disclosed. Among the new outputs of the subject disclosure are the continuous saturation and wettability profiles as a function of the pore sizes in the porous media. We demonstrate the use of this invention on a set of reservoir and outcrop carbonate core-plugs with a variety of laboratory controlled saturation and wettability conditions, along with a variety of core cleaning preparation techniques. The subject disclosure improves upon the existing methods used in the laboratory.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein:

FIGS. 3-1, 3-2 and 3-3 are schematic representations of different states of a triangular shaped pore, according to some embodiments;

FIGS. 5-1 and 5-2 are graphs of the $T_2$ distribution from inverse Laplace transform (ILT), the oil and water distributions, and wettability and saturation functions obtained from the inversion for a strongly oil-wet (W close to zero, i.e., most of the surface is covered by oil) rock example, according to some embodiments;

FIGS. 6-1 and 6-2 are graphs of the $T_2$ distribution from ILT and the oil and water distributions, and wettability and saturation functions obtained from the inversion for an example of a strongly water-wet plug at Swirr, according to some embodiments;

FIGS. 7-1 and 7-2 are graphs of the $T_2$ distribution from ILT and the oil and water distributions, and wettability and saturation functions obtained from the inversion for an example water-wet plug at $S_{or}$, according to some embodiments;

DETAILED DESCRIPTION

Figure 1:
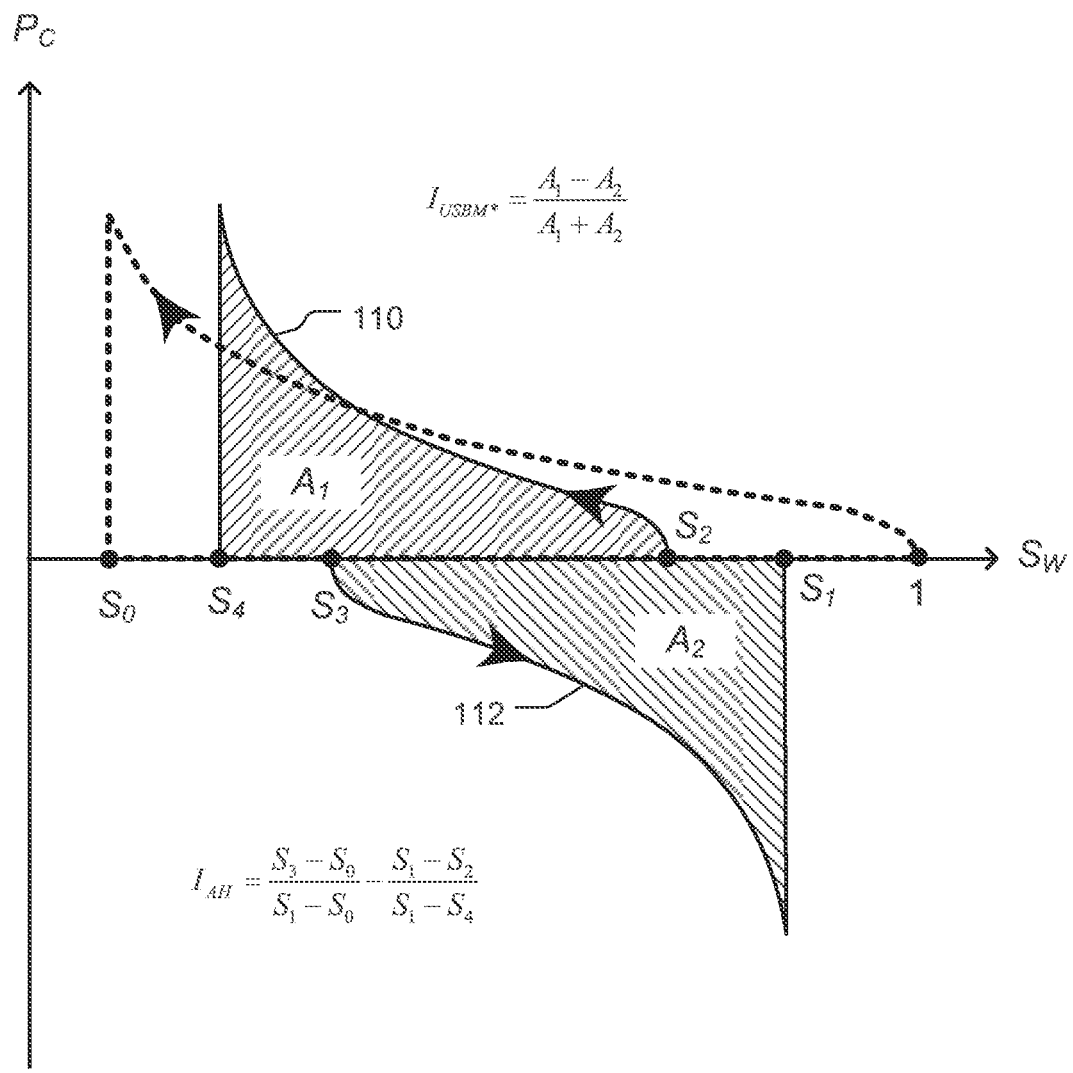
FIG. 1 illustrates a $P_C$ curve and definitions of the areas used to compute $I_{AH}$ and $I_{USBM}*$, according to some embodiments.

The particulars shown herein are by way of example and for purposes of illustrative discussion of the embodiments of the subject disclosure only, and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Wettability is an important parameter in the development of an oilfield (E Donaldson, R D Thomas, and P B Lorenz, "Wettability Determination and Its Effect on Recovery Efficiency," SPE Journal, (1969), 9, pp. 13-20; R A Salathiel, "Oil recovery by surface film drainage in mixed-wettability rocks," Journal of Petroleum Technology, (1973); W G Anderson, "Wettability Literature Survey—Part 6: The effects of Wettability on Waterflooding," Journal of Petroleum Technology, (1987); T Okasha, J Funk, and H Rashidi, "Fifty Years of Wettability Measurements in the Arab-D Carbonate Reservoir," Proceedings of SPE Middle East Oil and Gas Show and Conference, (March 2007), pp. 1-12), yet there are few methods of quantifying it. The two most common are the qualitative indices based on Pc curve measurements: (1) Amott-Harvey (AH), and (2) U.S. Bureau of Mines (USBM) methods.

According to some embodiments, an inversion technique is described that has been validated in the laboratory under a controlled set of conditions. Traditionally, such validation has been done by correlating the NMR wettability index under investigation against the various industry standards, and thereby determining whether the NMR method is valid. However, given the qualitative nature of the AH and USBM indices (See S Ma, X Zhang, N R Morrow, and X Zhou, "Characterization of wettability from spontaneous imbibition measurements," Journal of Canadian Petroleum Technology, (1999), 38 no. 13, p. 56), such benchmarking can be misleading. For a wide range of core plugs including native state, aged, and cleaned core plugs, it is shown herein that the NMR wettability index as described provides more information and is more consistent with the expected wettability based on well defined preparation methods.

A number of principles are used to extract wettability and saturation as a function of pore size from NMR $T_2$ data. The described method does not require that a pore geometry be specified, but instead is incorporated into the model by the measured, fully water-saturated relaxation ($T_2$) distribution. The method makes use of NMR data for two states of the core plug (for example, native and fully water saturated) and for two bulk fluid samples (for example, water and native oil). According to some embodiments, one output of the analysis is the native state $T_2$ distribution, which is decomposed into oil and water $T_2$ spectra, respectively. A second output is a wettability index as a function of the pore size spectrum. This index can be averaged over the pore size distribution to provide a single wettability index for the core plug on a −1 to +1 scale, consistent with the traditional convention.

The basic physics is that the NMR relaxation time $T_2$ of a fluid contained in a porous system is shortened from its bulk value as a result of surface interactions. In a pore system fully saturated and wetted by a single phase, the extent of relaxation enhancement is related to the pore diameter d as $T_2 \sim d$, i.e., smaller pores have shorter $T_2$. In the case of a mixed saturated pore system, the amount of $T_2$ shortening from surface relaxation for a given phase is directly proportional to the fraction of surface wetted by that phase. As a result, an unambiguous NMR wettability index for the rock can be derived from an average of the wettability across the pore system. The $T_2$ for a given phase in a pore also depends on the saturation of that phase in that pore. This implies that $T_2$ is sensitive to both wettability and saturation in the pore, as well as the pore size distribution itself.

To illustrate these principles, in a fully water-wet scenario, when a drop of oil is suspended in the water filled pore, the oil drop is isolated from the surface and therefore behaves as a bulk fluid with long $T_2$. Meanwhile, the $T_2$ of the water is shortened since the pore size for the water phase is effectively reduced by the presence of the suspended oil in the pore. A similar principle holds for the reverse situation of a water droplet suspended in an oil wet and oil saturated pore. These are the basic underlying principles which make up the forward model in the wettability model on which the described inversion is based.

Qualitative Interpretation from 2D NMR.

Figure 2:
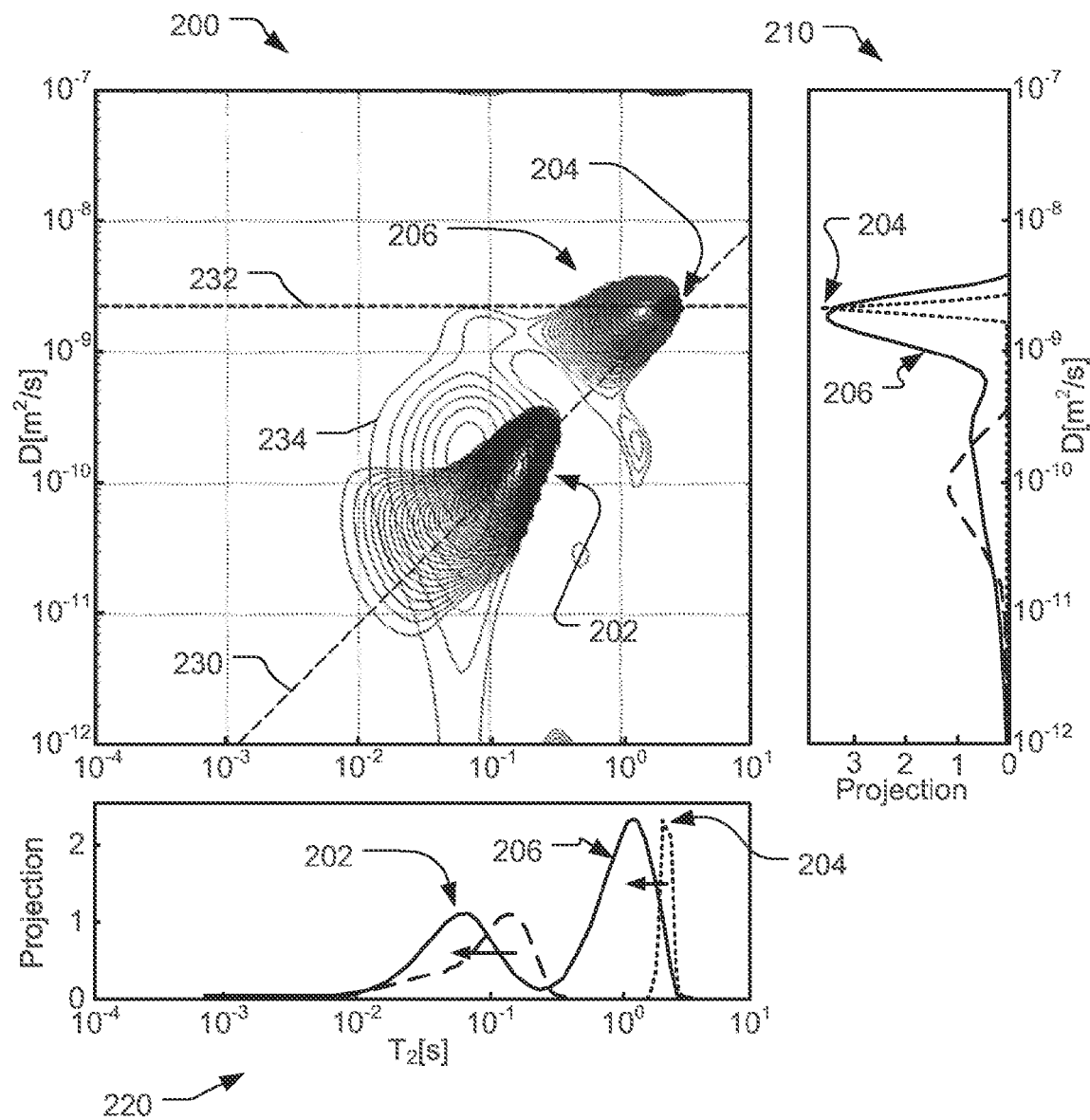
FIG. 2 shows plots of D-$T_2$ data from a representative case, according to some embodiments.

FIG. 2 shows plots of D-$T_2$ data from a representative case, according to some embodiments. Three D-$T_2$ distributions are presented in the main plot 200: (1) the bulk water peak 204, (2) the bulk dead crude oil distribution 202 which lies along the diagonal correlation line 230, and (3) the native state data for this plug 206. Note that although D-$T_2$ distributions are shown, according to some embodiments the described inversion can be obtained using only $T_2$. The data were taken at ambient conditions. The horizontal dashed line 232 corresponds to the water line, while the diagonal dashed line 230 corresponds to the dead crude oil correlation as described by S-W Lo, G J Hirasaki, W V House, and R Kobayashi, "Mixing rules and correlations of NMR relaxation time with viscosity, diffusivity, and gas/oil ratio of methane/hydrocarbon mixtures," SPE Journal, (2002), 7 no. 1, pp. 24-34. The two prominent features for the native state data are (1) the leftward shift of the signal from the bulk water peak 204, which corresponds to water wetting the rock, and, (2) a similar shift for the oil signal 202, which corresponds to crude oil wetting the rock.

Also shown in FIG. 2 are the $T_2$ projection plot 220 and the D projection plot 210. The arrows in the $T_2$ projection plot 220 show how wetting causes the bulk fluid responses to shift to the left, i.e., to shorter $T_2$, as a result of surface relaxation. It is significant that both fluids are found to shift to the left, which indicates that both fluids are to a certain extent wetting the pore surface. Therefore, according to D-$T_2$, this native state plug is qualitatively mixed-wet, which agrees well with the native state wettability indices ($I_{NMR}$, $I_{AH}$, $I_{USBM}^*$) which range between −0.3 and −0.2 for this case.

Advanced Interpretation: Wettability Inversion—Forward Model.

Figures 1, 3:
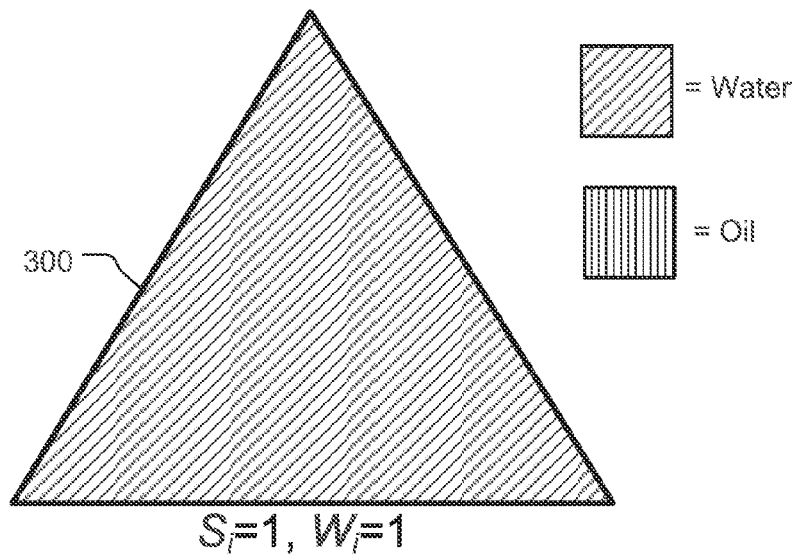
Figures 2, 3:
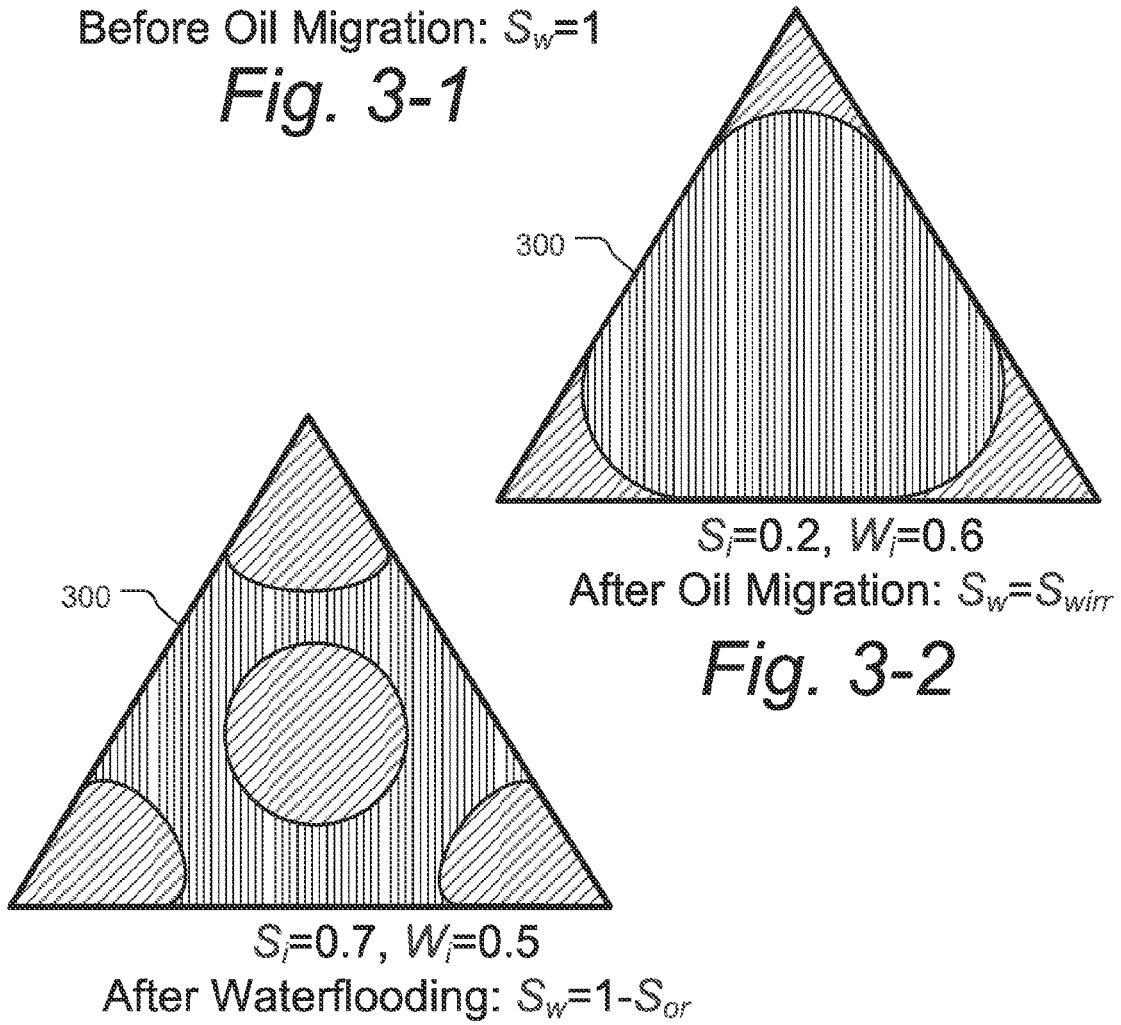
Figure 3:
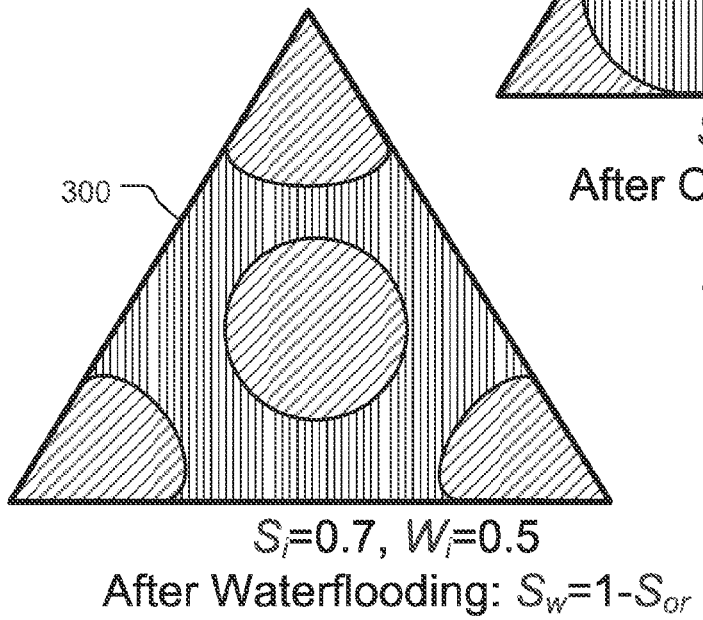

In order to understand the forward model in more detail, it is useful to first define what the saturation and wettability are at the pore scale. We define the saturation as $S_i$ and wettability as where the subscript i refers to the i'th pore of size i. In particular, $S_i$ is defined as the volume fraction of water in the i'th pore with surface relaxation time $T_{2S,i}(\propto d_i)$, which is bound by $0 \leq S_i \leq 1$. $W_i$ is defined as the surface fraction of that pore wall wetted by water, also bound by $0 \leq W_i \leq 1$. FIGS. 3-1, 3-2 and 3-3 are schematic representations of different states of a triangular shaped pore. In particular, FIG. 3-1 shows pore 300 after deposition, FIG. 3-2 shows pore 300 after oil migration, and FIG. 3-3 shows pore 300 after flushing caused by either a water based mud (WBM) filtrate invasion or water injection. FIGS. 3-1, 3-2 and 3-3 illustrate how $S_i$ and $W_i$ can vary inside a triangular pore during the geological lifetime of a reservoir rock. A systematic analysis of fluid distribution and flow in angular pores was provided by Ma et al., "Effect of contact angle on drainage and imbibition in regular polygonal tubes," Colloids and Surfaces A: Physicochemical and Engineering Aspects, (1996), 117 no. 3, pp. 273-291. The concavity/convexity of the oil/water interface arises from the balance between surface tension forces and viscous forces.

After the NMR $T_2$ inversion, the overall water saturation, $S_{NMR}$, and wettability index, $I_{NMR}$, for the whole plug are determined as functions of the average values of $S_i$ and $W_i$ over the pore spectrum $P(T_{2S,i})$ (i.e., the pore size distribution). The overall saturation is simply the average of $S_i$ weighted by the pore size distribution, while the wettability index is scaled to the traditional −1 to 1 interval.

$$S_{NMR} = \sum_i P(T_{2S,i}) S_i \quad (1)$$

$$I_{NMR} = 2\sum_i P(T_{2S,i}) W_i - 1 \quad (2)$$

The water saturation is bound by $0 \leq S_{NMR} \leq 1$, where $S_{NMR}=1$ implies 100% water saturated rock, while $S_{NMR}=0$ implies 100% oil saturated rock. The wettability index $I_{NMR}$ is bound by $-1 \leq I_{NMR} \leq 1$, where $I_{NMR}=1$ implies an entirely water-wet rock, $I_{NMR}=-1$ implies an entirely oil-wet rock, and $I_{NMR} \approx 0$ implies a neutral wettability of a mixed-wet rock. $T_{2,Si}$ is defined as the relaxation time due to surface relaxation inside the i'th pore, and $P(T_{2S})$ is normalized to 1. Note that we have distinguished between the surface relaxation $T_{2S}$ and the full relaxation time $T_2$ as such: $1/T_2 = 1/T_{2bulk} + 1/T_{2S}$, where $T_{2bulk}$ is the bulk relaxation component of the fluid without the presence of a pore surface. In order to limit the number of free parameters associated with $S_i$ and $W_i$, Looy-estijn et al. (See W. Looyestijn and J. Hofman, "Wettability Index Determination by Nuclear Magnetic Resonance," Proceedings of SPE Middle East Oil and Gas Show and Conference, (March 2005) and W J Looyestijn, S I Exploration, and P By, "Wettability Index Determination from NMR Logs," (April 2008), Petrophysics, pp. 130-145) proposed to represent the saturation $S_i$ and wettability $W_i$ by a function. We consider two types of functions:

(1) The original 4 parameter function proposed by Looyestijn et al. (See W. Looyestijn and J. Hofman, "Wettability Index Determination by Nuclear Magnetic Resonance," Proceedings of SPE Middle East Oil and Gas Show and Conference, (March 2005) and W J Looyestijn, S I Exploration, and P By, "Wettability Index Determination from NMR Logs," (April 2008), Petrophysics, pp. 130-145). This function is monotonic and characterized by two plateaus at short and long $T_{2S}$, and a smooth transition between the two plateaus. These functions reasonably match the expected distributions of fluids and wettabilities in native core plugs.

(2) A Gaussian function for the saturation $S_i$ allowing a non-monotonic saturation profile along the pore spectrum. Non-monotonic behavior in saturations may occur as a result of multiple drainage and imbibition events caused by tectonism and/or oilfield development.

Figure 4:
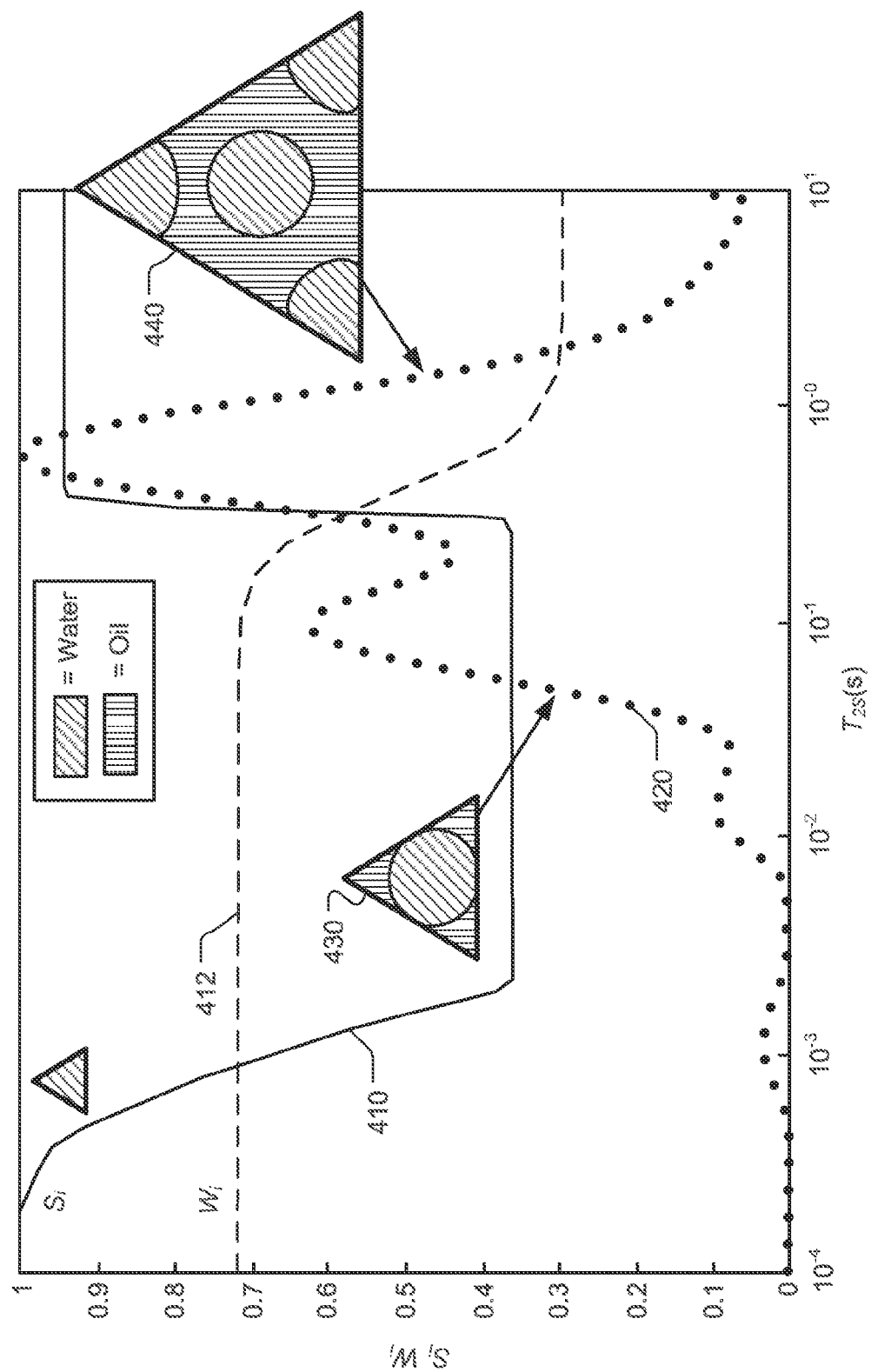
FIG. 4 illustrates a representative example of the forward model and inversion output for $S_i$ and $W_i$ across the pore spectrum data, according to some embodiments.

FIG. 4 illustrates a representative example of the forward model and inversion output for $S_i$ and $W_i$ across the pore spectrum data, according to some embodiments. $S_i$ (410) and wettability $W_i$ (412) across the pore spectrum data (420). The pore cartoons 430 and 440 illustrate how the big pores (440) would look according to $S_i$ and $W_i$ and similarly for the small pores (430). Note that the pore cartoons are meant as an illustration and do not correspond to the precise values of $S_i$, $W_i$ and pore size.

Inversion.

The theory of surface relaxation, including the one for wettability described herein, is presented in terms of relaxation times $T_2$. This makes the representation clearer and easier to understand. However, when we are dealing with real experimental data, we have to remember that the acquisition is done in the time domain. To express the results in the $T_2$ domain, an inversion (Inverse Laplace Transform, or ILT) is used (See L Venkataramanan, Y-Q Song, and M D Hürlimann, "Solving Fredholm integrals of the first kind with tensor product structure in 2 and 2.5 dimensions," IEEE Transactions on Signal Processing, (2002), 50 no. 5, pp. 1017-1026). This process is well known to be an ill posed problem without a unique solution. This problem is solved by the use of a regularization parameter which imposes a certain degree of smoothness to the $T_2$ distribution. This regularization parameter allows a stable solution at the price of details in the $T_2$ distribution. The use of a regularization parameter has proved to be fairly reliable and adequate for most applications in the oil industry, however, there is still an open question regarding the possibility of improving the data processing. Along these lines, according to some embodiments, we avoid the Laplace Inversion altogether following the same technique as described in L Venkataramanan, F K Gruber, T M Habashy, and D E Freed, "Mellin transform of CPMG data," Journal of Magnetic Resonance, (2010), 206 no. 1, pp. 20-31.

According to some embodiments, constraints are used in connection with the inversion. One example is an intelligent grid search method, which has the advantage of providing many solutions indexed by their overall quality of fitness to the data. A strength of the inversion is that we may easily introduce a constraint, such as described above, on the saturation $S_i$ across the pore spectrum in order to stabilize the inversion for wettability $W_i$ across the pore spectrum. The saturation constraint is based on the saturation history of the rock as well as some petrophysical insight into the problem. Table 1 shows four common reservoir scenarios dictating helpful saturation constraints without any loss of generality:

TABLE 1

Description of the different filters used in the inversion and petrophysical justifications.

| Saturation history and petrophysical insight | Saturation filter |
| --- | --- |
| Strongly oil wet rocks with the cycle $S_W = 0 \rightarrow (1 - S_{or})$ have been first saturated with oil and aged, and then flooded to $S_{or}$. Therefore one can assume that small pores are full of oil, while big pores contain more water. | $S_i$ monotonically increasing |
| Strongly water wet rocks with the cycle $S_W = 1 \rightarrow S_{wirr}$ have been saturated first with water, and then flooded to Swirr. Therefore one can assume that small pores are water filled, while big pores have more oil. | $S_i$ monotonically decreasing |
| Water-wet rocks with two cycles $S_W = 1 \rightarrow S_{wirr} \rightarrow (1 - S_{or})$ and oil-wet rocks with two cycles $S_W = 0 \rightarrow (1 - S_{or}) \rightarrow S_{wirr}$ have a Gaussian saturation profile where irreducible fluids in small pores $T_{2S} < 10^{-1}$s have not been displaced. Native state plugs affected by drilling mud fall into the first of these categories. | $S_i$ is a Gaussian profile centered in the large pores corresponding to $T_{2S} > 10^{-1}$s |
| The saturation index can be obtained independently from other techniques such as the amount of fluid production. | $S_{NMR}$ lies within +/−5% of an independent measurement |

NMR Wettability Inversion Results.

NMR wettability inversion can help to understand the complexity of wettability and saturation profiles at the pore scale. Three examples covering a wide variety of wettability types and saturation states are shown below:

Strongly oil-wet rock $S_W=0 \rightarrow (1-S_{or})$.

Figures 1, 5:
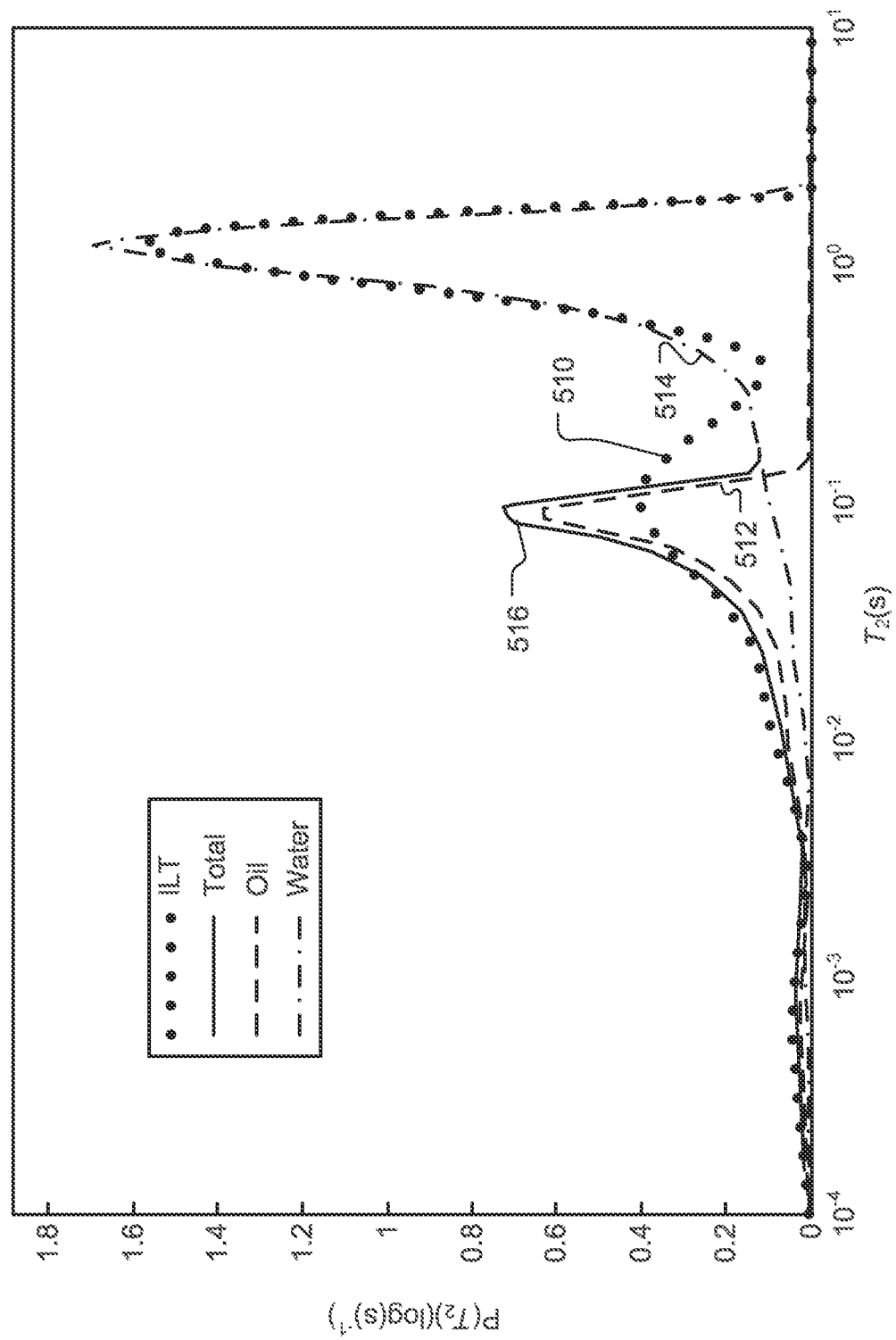
Figures 2, 5:
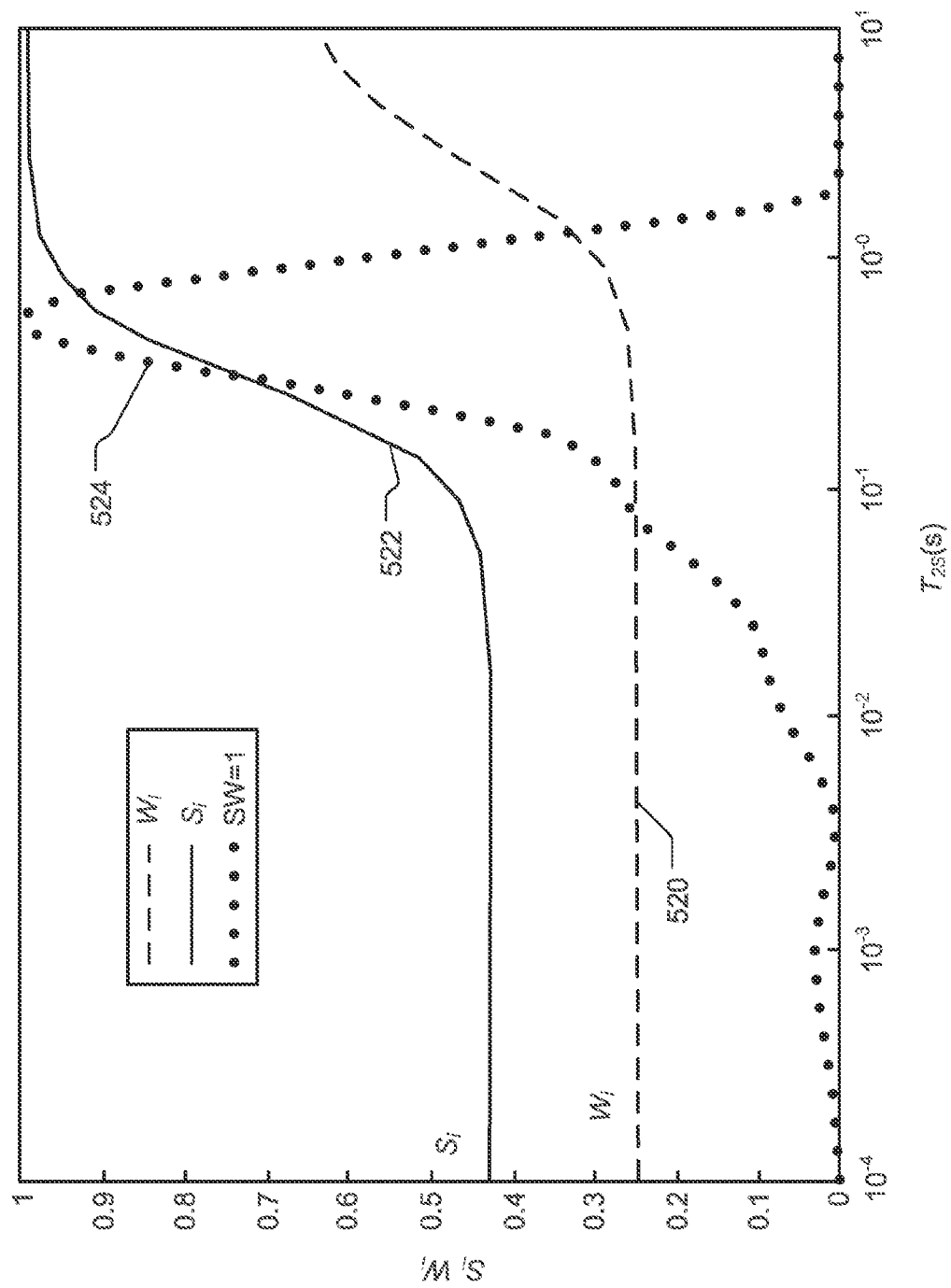

FIGS. 5-1 and 5-2 are graphs of the $T_2$ distribution from ILT and the oil and water distributions obtained from the inversion for a strongly oil-wet rock example, according to some embodiments. FIG. 5-1 plots the ILT (510) and the oil (512) and water (514) distributions along with the total (516). FIG. 5-2 plots the wettability ($W_i$) (520) and saturation ($S_i$) (522) functions obtained with the inversion together with the pore spectrum from SW=1 (524). The saturation steps at which the plug has been submitted before measuring the NMR response are $S_W=0 \rightarrow (1-S_{or})$. The overall water saturation is $S_{NMR}=0.74$ and the wettability index is $I_{NMR}=-0.47$. FIG. 5-1 clearly shows the presence of oil in the smaller pores ($T_2<10^{-1}$ s) and water in the larger ($T_2>10^{-1}$ s) pores. This is consistent with the history of the plug, that started fully oil saturated and has been desaturated by centrifuging with water. Note that the total (oil+water) fit has narrower and better-resolved peaks than the ILT. This is not an issue as such since the misfit from the inversion is calculated in the time domain (not shown), and furthermore, as already noted the ILT tends to artificially smooth out the solution in the $T_2$ domain as a result of regularization. In FIG. 5-2, the saturation function $S_i$ reflects the fluid distribution observed in the left panel. The wettability function $W_i$ stays very low for most of the range of $T_{2S}$ as expected for an oil-wet plug. We note that $W_i$ increases slightly in the range of $T_{2S}$ values where there are no data, therefore we do not speculate on this trend.

Strongly Water-Wet Rock $S_W=1 \rightarrow S_{wirr}$.

Figures 1, 6:
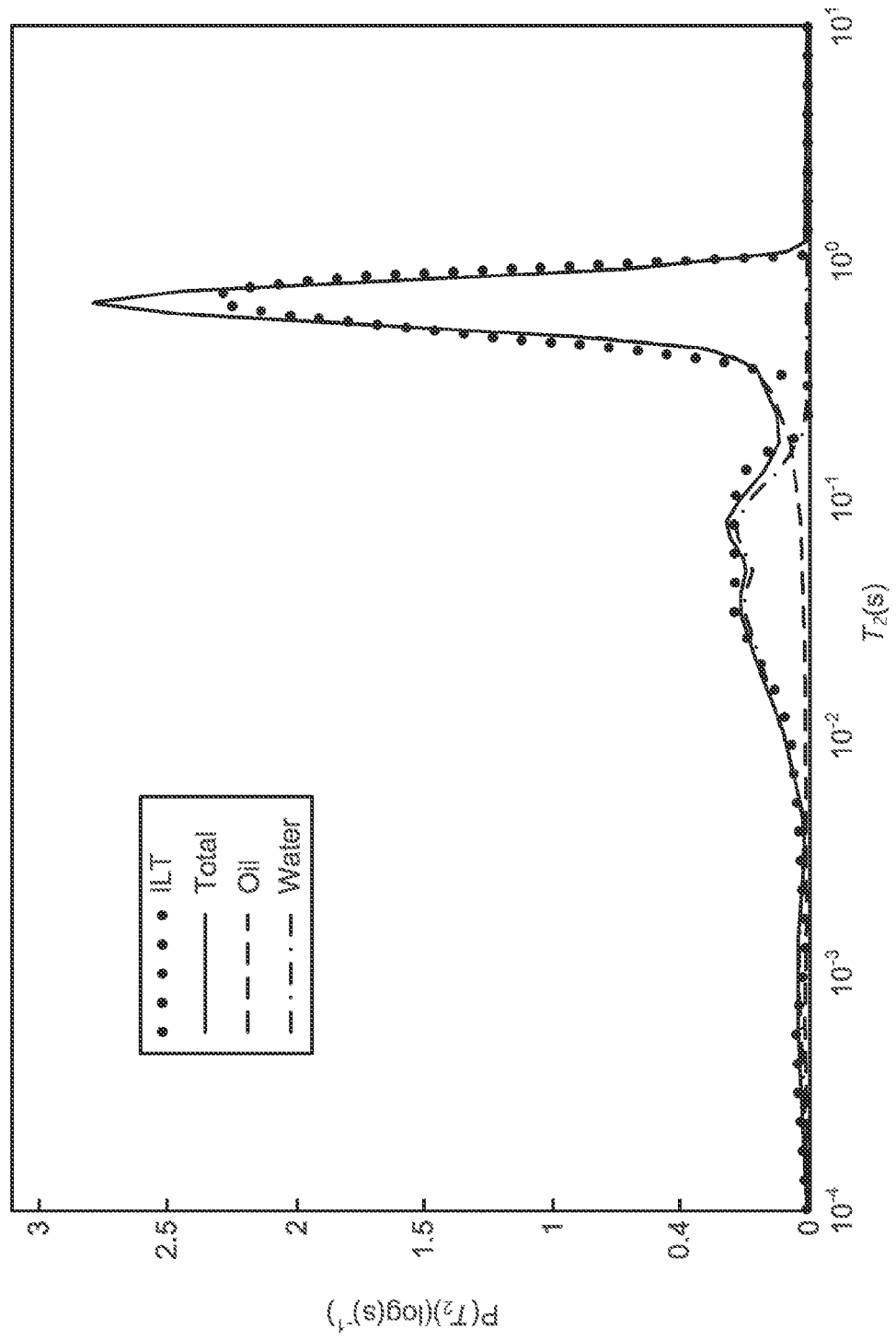
Figures 2, 6:
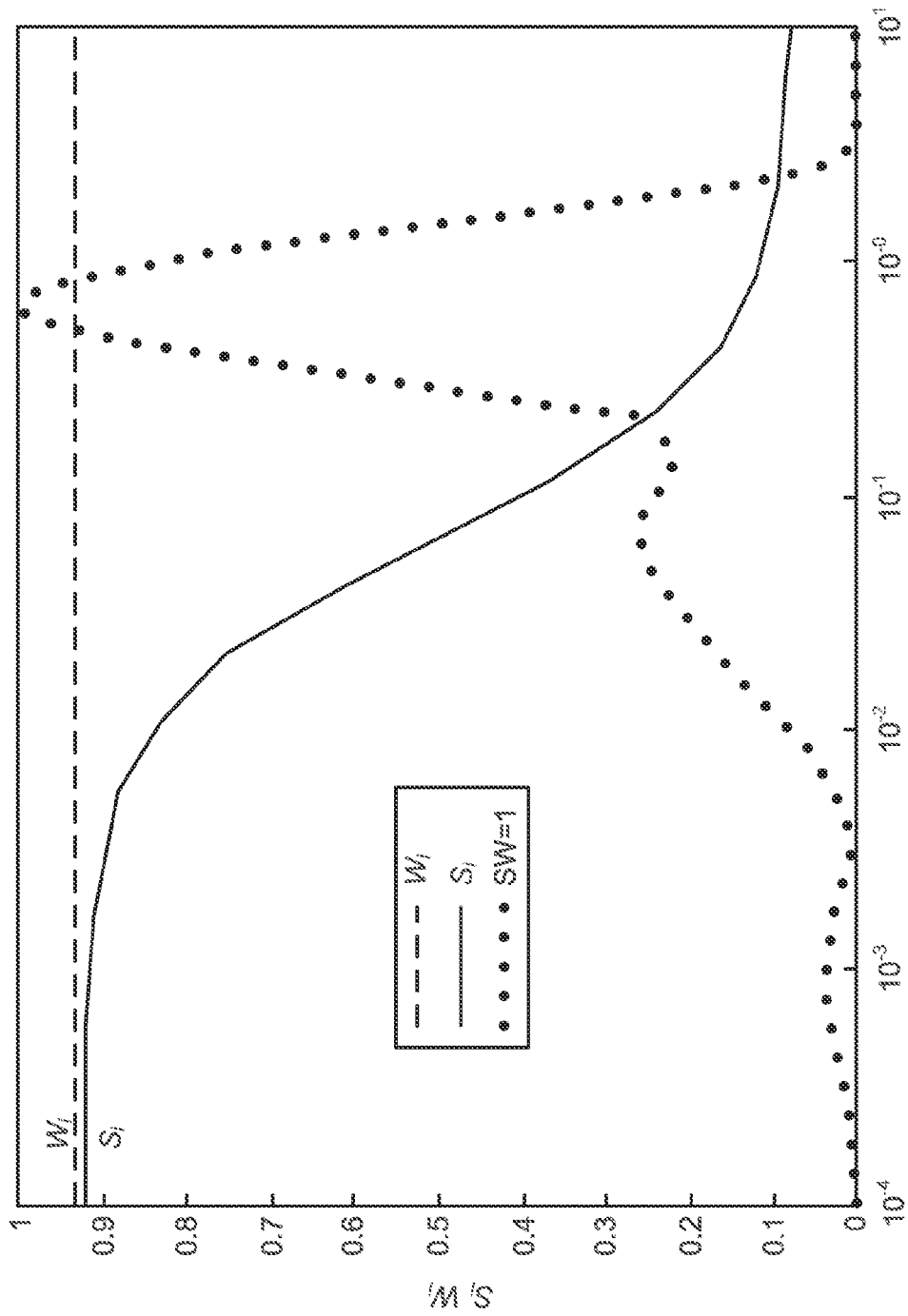

In FIGS. 6-1 (graph 610) and 6-2 (graph 612) we present a situation that is completely opposite to the one in FIGS. 5-1 and 5-2. FIGS. 6-1 and 6-2 are graphs of the $T_2$ distribution from ILT and the oil and water distributions obtained from the inversion for an example water-wet plug at Swirr, according to some embodiments. The saturation steps at which the plug has been submitted are $S_W=1 \rightarrow S_{wirr}$. The overall water saturation is $S_{NMR}=0.29$ and the wettability index is $I_{NMR}=+0.86$.

The oil and water distribution ranges are inverted and the wettability function is a constant at high values. These results are supported by the fact that the history of the plug is opposite too; the core-plug started from water saturated and was partially desaturated by oil. The forced cleaning used for this core plug also is consistent with the high wettability value.

Water-Wet Rock $S_W=1 \rightarrow S_{wirr} \rightarrow (1-S_{or})$.

Figures 1, 7:
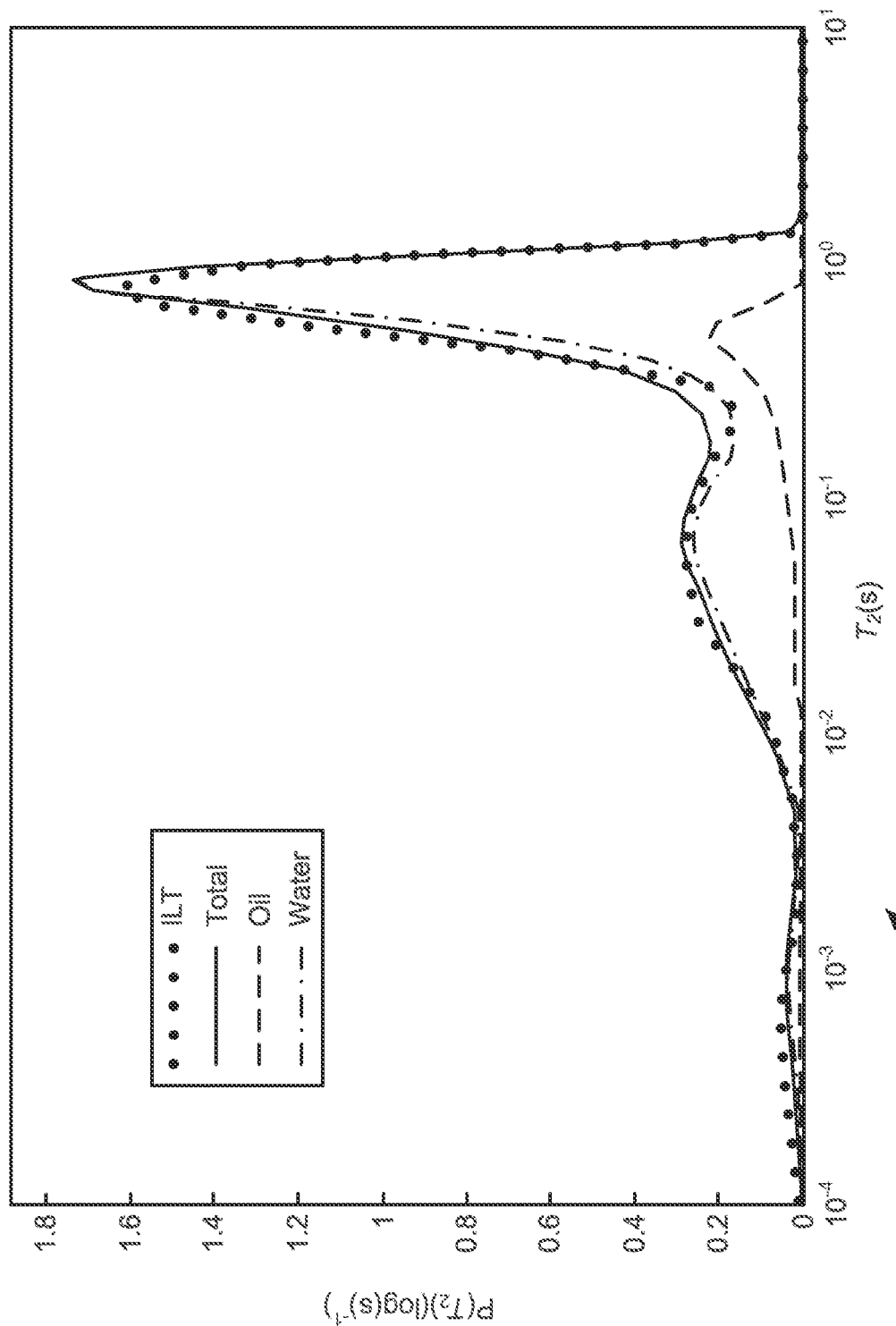
Figures 2, 7:
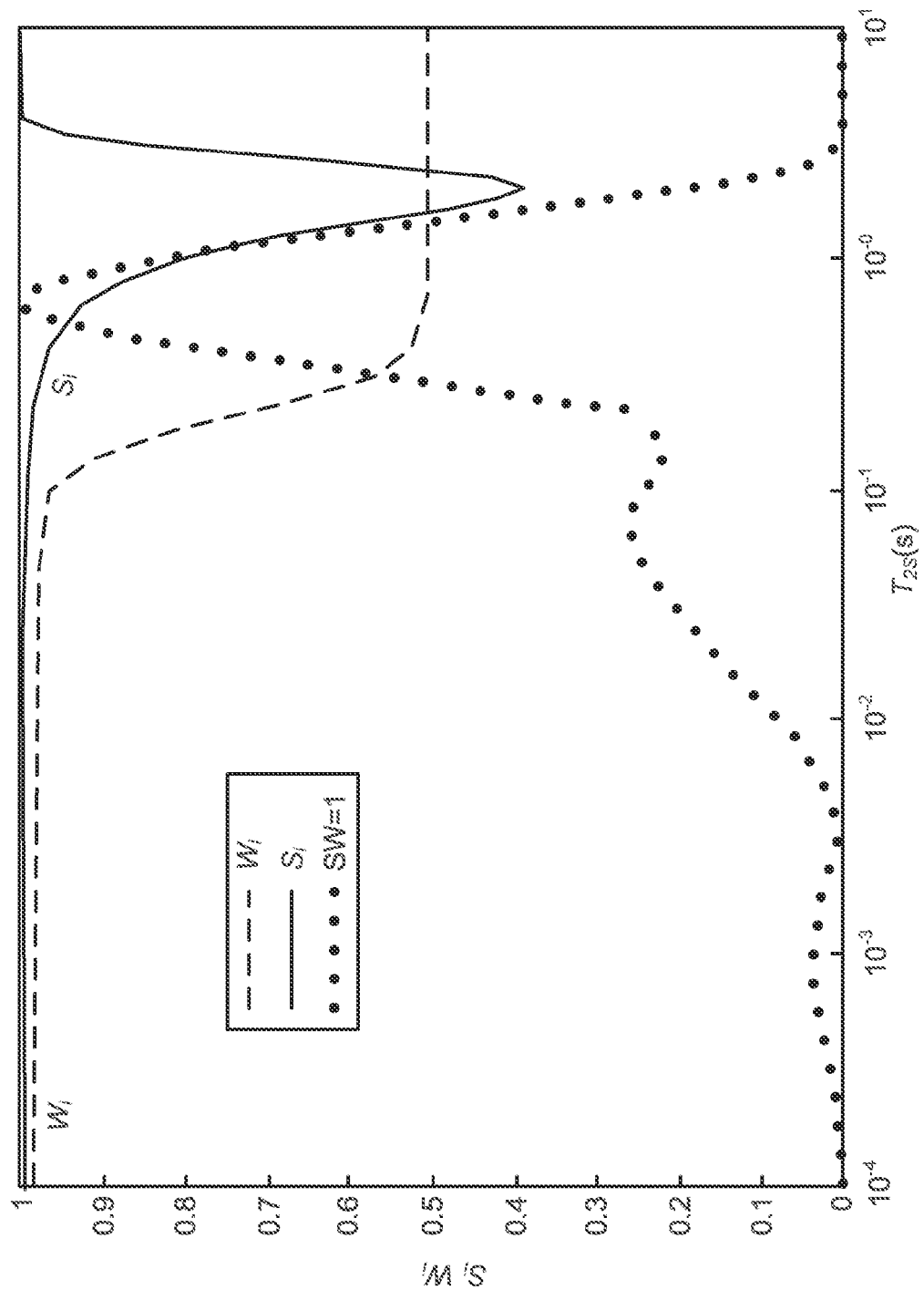

FIGS. 7-1 and 7-2 are graphs of the $T_2$ distribution from ILT and the oil and water distributions obtained from the inversion for an example water-wet plug at $S_{or}$, according to some embodiments. The saturation steps at which the plug has been submitted are $S_W=1 \rightarrow S_{wirr} \rightarrow (1-S_{or})$. For this solution the overall water saturation is $S_{NMR}=0.89$ and the wettability index from $I_{NMR}=+0.32$. FIG. 7-1 (graph 710) and FIG. 7-2 (graph 712) present the cases in which the plug has been exposed to two changes of saturation $S_W=1 \rightarrow S_{wirr} \rightarrow (1-S_{or})$ for the water wet plug. Because of this double change in saturation we adopted the inverted Gaussian profile for $S_i$. In this case the inverted Gaussian function helps in resolving oil trapped in the intermediate size pores. Similarly, for the oil wet plug exposed to two changes $S_W=0 \rightarrow (1-S_{or}) \rightarrow S_{wirr}$ (data not shown), the fluid distributions show water trapped in the intermediate pores corresponding to a Gaussian (not inverted) profile. Although the specific examples shown and described in FIGS. 5-1, 5-2, 6-1, 6-2, 7-1 and 7-2 illustrate a laboratory validating technique and demonstrate the benefits of having a saturation profile constrained by the saturation history, the specifics are not intended to be limiting.

According to some embodiments, new approaches to an NMR wettability inversion algorithm as well to the underlying forward model, both of which are applicable over a wide range of saturation and wettability conditions are described. The described approach takes the saturation history of the plug as well as some petrophysical insight into account to formulate a saturation filter on the set of solutions from the inversion, thereby stabilizing a solution set for the wettability across the pore spectrum. According to some embodiments, a new NMR inversion technique is incorporated which does not rely on an Inverse Laplace Transform or a regularization parameter, which further stabilizes the inversion algorithm for the wettability across the pore spectrum. These new techniques have been utilized on a set of reservoir and outcrop carbonate core-plugs with a variety of laboratory controlled saturation and wettability conditions, along with a variety of core cleaning preparation techniques. From knowledge of the wettability state following forced cleaning and outcrops, it has been found that the resulting NMR wettability index is more accurate than the industry standards in the case of water wet cores. Our findings suggest that a traditional one-to-one comparison of wettability indices is not a reliable way of benchmarking the various wettability techniques against each other. According to some embodiments, the described NMR wettability index is used as the measurement of choice for carbonate core plugs in the laboratory.

Figure 8:
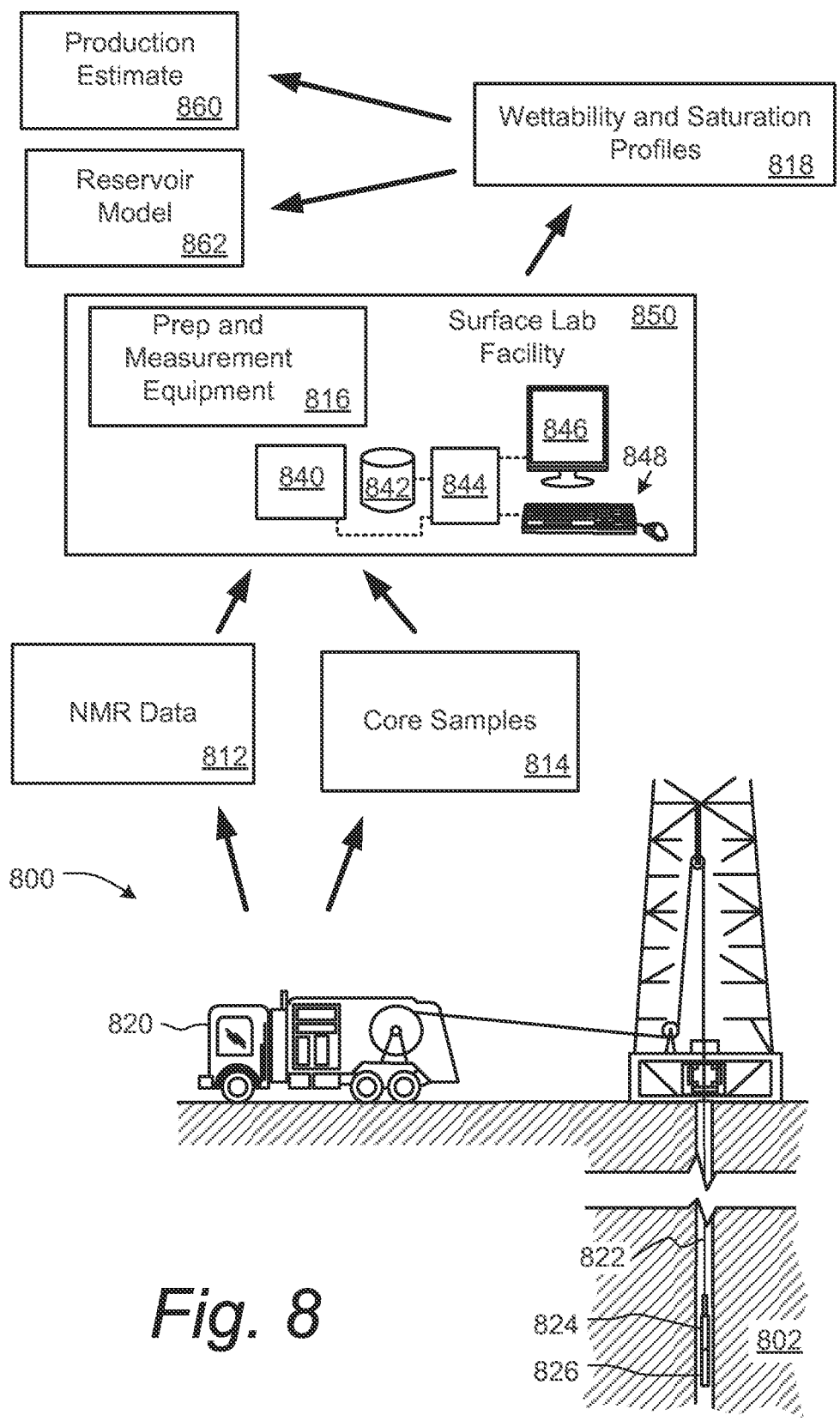
FIG. 8 is a diagram showing aspects of a system for determining wettability and saturation profiles from NMR data, according to some embodiments.

FIG. 8 is a diagram showing aspects of a system for determining wettability and saturation profiles from NMR data, according to some embodiments. Core samples are being gathered from a subterranean rock formation 802 at wellsite 800 via a wireline truck 820 deploying a wireline tool string in a well via wireline 822. The tool string includes one or more wireline tools including a core sampling tool 824, and/or an NMR tool 826. The acquired core sample 814 is transported from the wellsite 800 to a surface facility 850, which includes one or more central processing units 844 for carrying out the data processing procedures as described herein, as well as other processing. Facility also includes a data storage system 842, communications and input/output modules 840, a user display 846 and a user input system 848. According to some embodiments, the surface facility 850 may be located in a location remote from the wellsite 800. According to some embodiments, borehole NMR measurements are made of the fluids and rock in formation 802 and the resulting NMR data 812 is transmitted to the surface lab facility 850. According to some embodiments, the NMR tool 826 and/or the core sampling tool 824 are configured and adapted to be deployed in a bottom hole assembly and make measurements and/or obtain core samples during a drilling operation.

Surface facility 850 also includes preparation and measurement equipment 816 which is adapted and configured to carry out the core preparation and various measurement procedures such as described herein to results such as wettability and saturation profiles 818 which can then be used for purposes such as enhancing a production estimate 860 and/or reservoir model 862.

Figure 9:
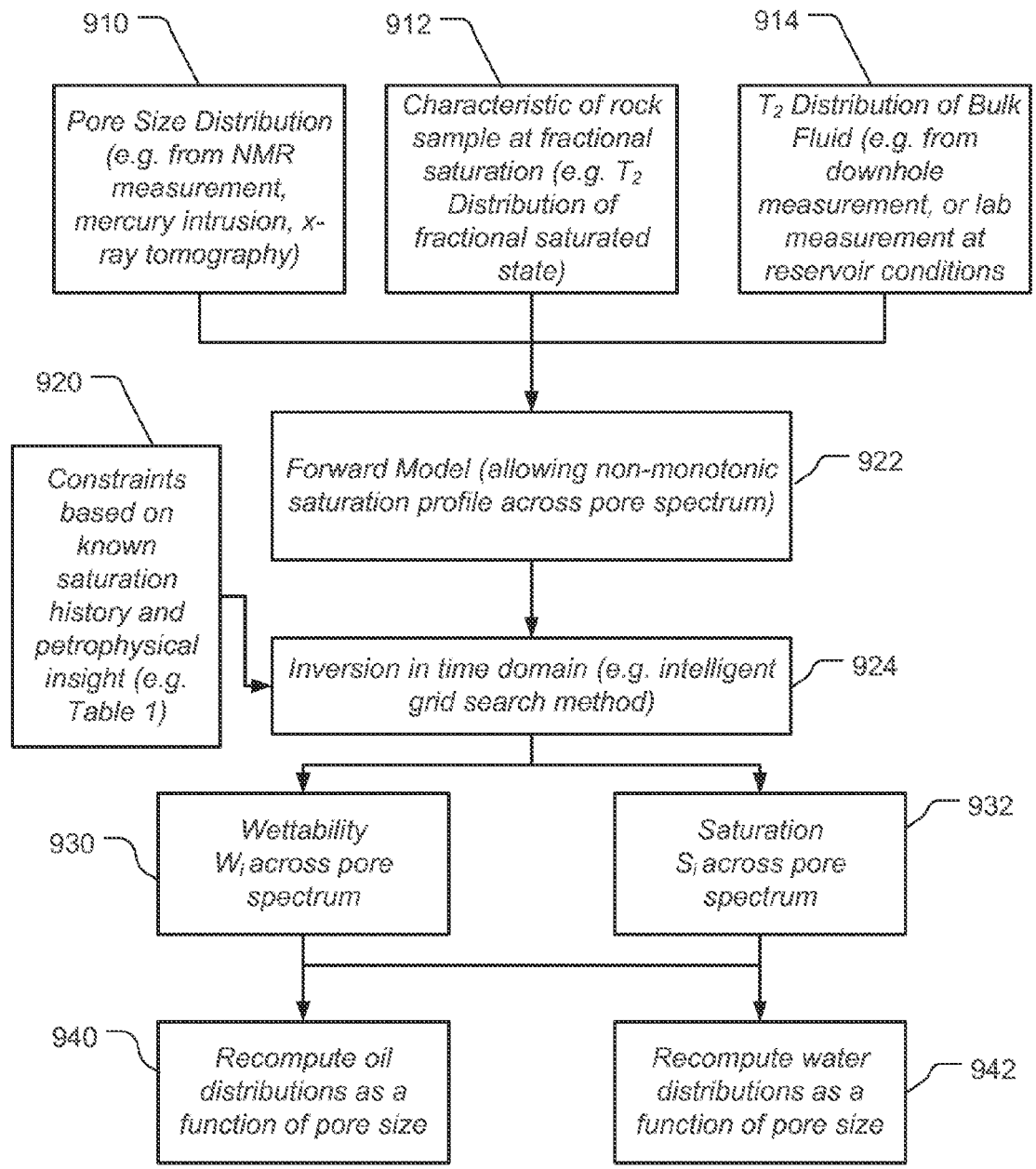
FIG. 9 is a block diagram showing aspects of methods for determining wettability and saturation profiles from NMR data, according to some embodiments.

FIG. 9 is a block diagram showing aspects of methods for determining wettability and saturation profiles from NMR data, according to some embodiments. In block 910, pore size distribution data is obtained using a technique such as NMR measurements on the solid sample. According to some embodiments, other methods can be used to obtain the pore size distribution, such as a mercury intrusion method, which can be particularly useful in cases where the sample is relatively homogeneous, such as sandstone. Another known method for obtaining the pore size distribution is digital rock images such as x-ray tomographic methods. In block 912, one or more characteristics of mixed-state fluid (e.g., oil) determined from the rock sample. Examples include $T_2$ distribution data determined from rock samples in a fractionally saturated state (i.e., containing both oil and water). In block 914, an third input is $T_2$ distribution data of one of the bulk fluids, for example the oil. According to some embodiments, this measurement can be performed downhole using a wellbore deployable NMR tool, or according to other embodiments, this can be performed using laboratory measurements at reservoir conditions. According to some embodiments, lab measurements can be corrected for the reservoir conditions, or a simulated response for the bulk fluids at reservoir conditions can be used. In block 922 the inputs shown blocks 910, 912 and 914, are used in a forward model, which include a function for saturation that is non-monotonically increasing or decreasing along a spectrum of pore sizes. In block 924 an inversion is performed on the forward model. According to some embodiments, the inversion is performed in the time domain. The inversion can be carried out with mathematical constraints 920 on the saturation values, for example based on known saturation history and/or petrophysical insight. The inversion yields a wettability $W_i$ profile 930 and/or a saturation $S_i$ profile 932, which can be in the form of oil distributions as a function of pore size 940 and/or water distributions as a function of pore size 942. According to some embodiments, from pore size distribution data 910 and the wettability $W_i$ profile 930 the overall wettability for the sample can be calculated. Similarly, from pore size distribution data 910 and the saturation $S_i$ profile 932 the overall saturation for the sample can be calculated. Note that while the oil and water distributions 940 and 942 are technically encompassed in the inversion block 924, they can be re-computed according to some embodiments. Additionally, according to some embodiments, the overall water saturation, $S_{NMR}$, and wettability index, $I_{NMR}$, for the whole plug are determined as functions of the average values of $S_i$ and $W_i$ over the pore spectrum $P(T_{2S,i})$ (i.e., the pore size distribution).

According to some embodiments, the techniques described herein are applicable beyond the oilfield industry. In general, the techniques described herein can be applied wherever porous media applications are important, for example in the medical, pharmaceutical, materials science, construction, aerospace, and environmental industries. Examples of applications for the described techniques include: bone research, drug delivery methods, novel materials development, improved construction materials such as cements, lighter aircraft wings, and spill cleanup.

Although only some example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method for characterizing wettability of a porous media, the method comprising:
    Receiving pore size distribution data representing a distribution of pore sizes within the porous media;
    Receiving nuclear magnetic resonance (NMR) data from a bulk aqueous fluid;
    Receiving nuclear magnetic resonance (NMR) data from a bulk oil; and
    performing an inversion on the nuclear magnetic resonance (NMR) data using a forward model for pore level distribution of wettability and saturation in mixed wet conditions over a plurality of pore sizes using the pore size distribution data and the nuclear magnetic resonance (NMR) data for the bulk aqueous fluid and bulk oil, thereby generating a wettability profile across a pore spectrum for the aqueous and/or oil fluids over a plurality of pore sizes of the porous media.

2. The method according to claim 1, wherein the nuclear magnetic resonance (NMR) data is nuclear magnetic resonance (NMR) echo train data and the inversion is performed in the time domain.

3. The method according to claim 1, wherein the NMR data is of a type selected from a group consisting of: Car-Purcell-Miniboom-Gill (CPMG), diffusion editing, $T_1$-$T_2$, $T_2$, $T_2$-$T_2$, D-$T_1$ and D-$T_2$, where T1 is a longitudinal relaxation time, T2 is a transverse relaxation time, and D is an indication of diffusion.

4. The method according to claim 1, wherein the forward model includes a function for saturation that is non-monotonically increasing or decreasing along a spectrum of pore sizes.

5. The method according to claim 1, wherein the performing of the inversion includes using a grid search method for the inversion.

6. The method according to claim 1, wherein the performing of the inversion includes mathematically constraining saturation values across a plurality of pore sizes in the forward model.

7. The method according to claim 6, wherein the saturation values are constrained based at least in part on a known saturation history of the porous media.

8. The method according to claim 7, wherein the porous media was originally strongly oil-wet and then flooded with the aqueous fluid, the water saturation is constrained to be monotonically increasing with increasing pore size.

9. The method according to claim 7, wherein the porous media was originally strongly water-wet and then flooded with oil, the water saturation is constrained to be monotonically decreasing with increasing pore size.

10. The method according to claim 7, wherein the porous media has experienced an oil flooding and water flooding event, the water saturation is constrained to a Gaussian profile.

11. The method according to claim 7, wherein the saturation history is known by virtue of a saturation technique selected from a group consisting of: core flooding, core centrifuge, reservoir management, water flooding history, and production history.

12. The method according to claim 7, wherein a saturation index is obtained from an independent measurement, and an overall water saturation $S_{NMR}$ is constrained to be within a fixed range of the independent measurement.

13. The method according to claim 6, wherein the saturation is known by injecting a paramagnetic fluid into the porous media.

14. The method according to claim 1, wherein the performing of the inversion includes mathematically constraining the forward model using data derived from nuclear magnetic resonance (NMR) data.

15. The method according to claim 14, wherein data is derived using a Mellin transform.

16. The method according to claim 1, wherein in the performing of the inversion further generates a saturation profile across a pore spectrum.

17. The method according to claim 16, further comprising determining overall wettability by integrating the wettability profile weighted by the pore size distribution data; and determining overall saturation by integrating the saturation profile weighted by the pore size distribution data.

18. The method according to claim 16, further comprising displaying to a user said wettability and saturation profiles as a function of pore size distribution.

19. The method according to claim 1, wherein the porous media is a core sample from a subterranean hydrocarbon-bearing rock formation.

20. The method according to claim 1, wherein the pore size distribution data is obtained using a technique selected from a group consisting of: nuclear magnetic resonance (NMR) $T_2$ pore size distribution; mercury intrusion; and x-ray tomography.

21. A system for characterizing wettability of a porous media, the system comprising:
an nuclear magnetic resonance (NMR) measurement system adapted and configured to make nuclear magnetic resonance (NMR) measurements of a bulk aqueous fluid and a bulk oil, and to generate therefrom nuclear magnetic resonance (NMR) data; and
a processing system programmed and configured to perform an inversion on the nuclear magnetic resonance (NMR) data using a forward model for pore level distribution of wettability and saturation in mixed wet conditions over a plurality of pore sizes using a pore size distribution of the porous media, and the nuclear magnetic resonance (NMR) data, thereby generating a wettability profile across a pore spectrum for the aqueous fluid over a plurality of pore sizes of the porous media.

22. The system according to claim 21, wherein the nuclear magnetic resonance (NMR) data is echo train data and the inversion is performed in the time domain.

23. The system according to claim 21, wherein the porous media is a core sample from a subterranean hydrocarbon-bearing formation.

24. The system according to claim 23, further comprising a core sampling tool deployable in a wellbore configured to obtain a core samples from the subterranean formation.

25. The system according to claim 21, wherein at least part of the nuclear magnetic resonance (NMR) measurement system is adapted to be deployed downhole so as to make the nuclear magnetic resonance (NMR) measurements of the bulk aqueous fluid and/or bulk oil downhole while the fluid is in a live state.

26. The system according to claim 21, wherein the inversion on the nuclear magnetic resonance (NMR) data further generates a saturation profile across the pore spectrum and wherein the processing system is further configured to displaying to a user said wettability and saturation profiles as a function of pore size distribution.

27. A method for characterizing wettability of a porous media by a first fluid in the presence of a second fluid, the method comprising:
receiving nuclear magnetic resonance (NMR) data from the first and the second bulk fluids;
receiving pore size distribution data representing a distribution of pore sizes within the porous media; and
performing an inversion process in the time domain using the nuclear magnetic resonance (NMR) data using a forward model for pore level distribution of wettability and saturation in mixed wet conditions over a plurality of pore sizes using the pore size distribution data and the nuclear magnetic resonance (NMR) each train data, thereby generating a wettability profile across a pore spectrum for the first fluid over a plurality of pore sizes of the porous media.

28. The method according to claim 27, wherein nuclear magnetic resonance (NMR) data is nuclear magnetic resonance (NMR) echo train data and the inversion process is performed in the time domain.

29. The method according to claim 27, wherein the nuclear magnetic resonance (NMR) data is of a type selected from a group consisting of: Car-Purcell-Meiboom-Gill (CPMG), diffusion editing, $T_1$-$T_2$, $T_2$, $T_2$-$T_2$, D-$T_1$ and D-$T_2$ where T1 is a longitudinal relaxation time, T2 is a transverse relaxation time, and D is an indication of diffusion.

30. The method according to claim 27, wherein the performing of the inversion includes mathematically constraining saturation values across a plurality of pore sizes in the forward model.

31. The method according to claim 27, wherein the performing of the inversion includes using a Mellin transform.

32. The method according to claim 31, wherein the performing of the inversion includes mathematically constraining saturation values across a plurality of pore sizes in the forward model based at least in part on a known saturation history of the porous media.

33. The method according to claim 32, wherein the saturation is known by injecting a paramagnetic fluid into the porous media.

34. The method according to claim 31, wherein in the performing of the inversion further generates a saturation profile across a pore spectrum.

35. The method according to claim 31, wherein the porous media is a rock sample from a subterranean hydrocarbon bearing, the first fluid is aqueous and second fluid is an oil.

* * * * *